(12) United States Patent
Rahn (10) Patent No.: US 8,507,294 B2
(45) Date of Patent: Aug. 13, 2013

(54) METHOD AND SYSTEM FOR ANALYTE MONITORING USING SURFACE PLASMONS WITH A REFRESHABLE SURFACE

(75) Inventor: John Richard Rahn, Sammamish, WA (US)

(73) Assignee: Empire Technology Development LLC, Wilmington, DE (US)

( * ) Notice: Subject to any disclaimer, the term of this patent is extended or adjusted under 35 U.S.C. 154(b) by 21 days.

(21) Appl. No.: 13/500,052

(22) PCT Filed: Jul. 13, 2011

(86) PCT No.: PCT/US2011/043863
§ 371 (c)(1),
(2), (4) Date: Apr. 3, 2012

(87) PCT Pub. No.: WO2013/009308
PCT Pub. Date: Jan. 17, 2013

(65) Prior Publication Data
US 2013/0017622 A1 Jan. 17, 2013

(51) Int. Cl.
*G01N 21/55* (2006.01)
(52) U.S. Cl.
USPC ............................................ 436/501; 422/69
(58) Field of Classification Search
None
See application file for complete search history.

(56) References Cited

U.S. PATENT DOCUMENTS

| 5,492,840 | A | * | 2/1996 | Malmqvist et al. | 436/518 |
|---|---|---|---|---|---|
| 5,822,472 | A | * | 10/1998 | Danielzik et al. | 385/12 |
| 6,750,065 | B1 | | 6/2004 | White et al. | |
| 6,950,184 | B2 | | 9/2005 | Stewart et al. | |
| 7,333,197 | B2 | | 2/2008 | Fritz et al. | |
| 7,605,916 | B2 | | 10/2009 | Zhang et al. | |
| 2002/0128234 | A1 | * | 9/2002 | Hubbell et al. | 514/100 |
| 2002/0171841 | A1 | * | 11/2002 | Elkind et al. | 356/445 |
| 2004/0046963 | A1 | * | 3/2004 | Lackritz et al. | 356/445 |
| 2004/0180379 | A1 | | 9/2004 | Van Duyne et al. | |
| 2008/0193965 | A1 | | 8/2008 | Zeng et al. | |
| 2009/0225310 | A1 | | 9/2009 | Yang et al. | |
| 2009/0303472 | A1 | | 12/2009 | Zhao et al. | |
| 2010/0055721 | A1 | | 3/2010 | Lambert et al. | |
| 2010/0087723 | A1 | | 4/2010 | Van Duyne et al. | |
| 2010/0210029 | A1 | | 8/2010 | Meinhart et al. | |
| 2010/0248283 | A1 | * | 9/2010 | Xiao et al. | 435/29 |

OTHER PUBLICATIONS

GE Healthcare, "BIACORE," printed on Dec. 21, 2011, retrieved from http://www.biacore.com/lifesciences/index.html, 1 page.

(Continued)

*Primary Examiner* — Mark Shibuya
*Assistant Examiner* — R. (Trey) Barlow, III
(74) *Attorney, Agent, or Firm* — Foley & Lardner LLP (57) ABSTRACT

The present technology provides an illustrative method for analyte monitoring using surface plasmons with a refreshable surface. The method includes placing a solution to be monitored in contact with a working surface of a surface plasmon resonance (SPR) generation system. The working surface includes a metal surface disposed on a glass surface, and the metal surface includes a first binding substance that provides binding sites for an analyte. The method further includes applying light to the metal surface at a plurality of angles over a period of time, measuring a reflectance of the light at each of the plurality of angles to determine an SPR angle, and monitoring changes to the SPR angle over the period of time. The working surface of the SPR generation system is refreshed by depositing a new layer of the first binding substance on the working surface of the SPR generation system.

18 Claims, 6 Drawing Sheets

(56) References Cited

OTHER PUBLICATIONS

Choi, S. et al., "A regenerative biosensing surface in microfluidics using electrochemical desorption of short-chain self-assembled monolayer," Microfluidics and Nanofluidics, 2009, vol. 7, pp. 819-826.

Garcia-Ramos, J.V. et al., "Plasmonic Metal Nanoparticle Functionalization for Selective Sensing of Persistent Pollutants by Surface-enhanced Raman Scattering," Can. J. Anal. Sci. Spec., 2007, vol. 52, No. 3, pp. 186-197.

Genson, K. et al., "Langmuir—Blodgett Monolayers of Gold Nanoparticles with Amphiphilic Shells from V-Shaped Binary Polymer Arms", Langmuir, 2006, vol. 22, 7011-7015.

Guerrini, L., "Plasmonic Metal Nanoparticle Functionalization for Selective Sensing of Persistent Pollutants by SERS," SERS roundtable, Oct. 3-5, 2007, Poltesrdorf, Germany, printed on Mar. 27, 2012, retrieved from http://www.fkphy.uni-duesseldorf.de/Guerrini.pdf, 36 pages.

Guerrini, L. et al., "Self-assembly of a dithiocarbamate calix[4]arene on Ag nanoparticles and its application in the fabrication of surface-enhanced Raman scattering based nanosensors," Phys. Chem. Chem. Phys., 2009, vol. 11, pp. 1787-1793.

International Search Report and Written Opinion for PCT/US2011/043863 mailed Sep. 14, 2011.

Karlsson, R. et al., "Surface Plasmon Resonance Detection and Multispot Sensing for Direct Monitoring of Interactions Involving Low-Molecular-Weight Analytes and for Determination of Low Affinities," Anal. Biochem., 1995, vol. 228, pp. 274-280.

Kneipp, K. et al., "Extremely Large Enhancement Factors in Surface-Enhanced Raman Scattering for Molecules on Colloidal Gold Clusters," Appl. Spectrosc., 1998, vol. 52, No. 12, pp. 1493-1497.

Kneipp, K. et al., "Single Molecule Detection Using Surface-Enhanced Raman Scattering (SERS)," Phys. Rev. Lett., Mar. 3, 1997, vol. 78, No. 9, pp. 1667-1670.

Lyon, L.A. et al., "Colloidal Au-Enhanced Surface Plasmon Resonance Immunosensing," Anal. Chem., Dec. 15, 1998, vol. 70, No. 24, pp. 5177-5183.

Mayo, C.S. et al., "Apparatus for the study of macromolecular adsorption," Rev. Sci. Instrum., Apr. 1989, vol. 60, No. 4, pp. 739-745.

Moskovits, M., "Surface-enhanced spectroscopy," Rev. Mod. Phys., Jul. 1985, vol. 57, No. 3, pp. 783-826.

Rahn, J.R. et al., "Antibody Binding to Antigen-Coated Substrates Studied with Surface Plasmon Oscillations," Langmuir, 1995, vol. 11, No. 2, pp. 650-654.

Rahn, J.R., "Adsorption of Macromolecules onto Functionalized Surfaces," PhD Dissertation, University of Massachusetts, Feb. 1996, 202 pages.

Raether, H., "Surface Plasmons on Smooth and Rough Surfaces," Springer Tracts in Modern Physics, 1988, vol. 111, pp. 4-13, 16-25, 40-41, and 118-123.

Sanchez-Cortes, S. et al., "Raman and surface-enhanced Raman spectroscopy of dithiocarbamate fungicides," Vib. Spectrosc., 1998, vol. 17, pp. 133-139 and 142-144.

Shankaran, D.R. et al., "Recent advancements in surface plasmon resonance immunosensors for detection of small molecules of biomedical, food and environmental interest," Sensors and Actuators B: Chemical, 2007, vol. 121, pp. 158-177.

Trinh, L.T.T. et al., "Slow salt-induced aggregation of citrate-covered silver particles in aqueous solutions of cellulose derivatives," Colloid Polym. Sci., 2009, vol. 287, pp. 1391-1404.

Werts, M.H.V. et al., "Nanometer Scale Patterning of Langmuir-Blodgett Films of Gold Nanoparticles by Electron Beam Lithography," Nano Letters, 2002, Published on Web Dec. 11, 2001, vol. 2, No. 1, pp. 43-47.

* cited by examiner

METHOD AND SYSTEM FOR ANALYTE MONITORING USING SURFACE PLASMONS WITH A REFRESHABLE SURFACE

CROSS-REFERENCE TO RELATED APPLICATIONS

The present application is a U.S. national stage application claiming the benefit of International Application No. PCT/US2011/043863, filed on Jul. 13, 2011, the entire contents of which are incorporated herein by reference in their entirety.

BACKGROUND

The following description is provided to assist the understanding of the reader. None of the information provided or references cited is admitted to be prior art.

Pollutants are present throughout the environment, and accordingly, the ability to detect and identify trace quantities of pollutants has become increasingly important. For many pollutants, a high degree of sensitivity is required because dangerous concentrations may exist at levels as low as a few parts per billion (ppb). Examples of situations requiring such high degrees of sensitivity range from analyses of pollutants in groundwater to analysis of cancer treatment drugs in blood serum.

SUMMARY

The present technology provides an illustrative method for analyte monitoring using surface plasmons with a refreshable surface. The method includes providing a solution to be monitored for the analyte and placing the solution to be monitored in contact with a working surface of a surface plasmon resonance (SPR) generation system. The working surface includes a metal surface disposed on a glass surface, and the metal surface includes a first binding substance that provides binding sites for the analyte. The method also includes applying light to the metal surface at a plurality of angles over a period of time, measuring a reflectance of the light at each of the plurality of angles to determine an SPR angle, and monitoring changes to the SPR angle over the period of time to determine if an amount of the analyte within the solution to be monitored exceeds a predetermined threshold amount of the analyte. The amount of the analyte within the solution to be monitored exceeds the predetermined threshold amount of the analyte if a detected decrease in a rate of change of the SPR angle occurs sooner than a predetermined threshold time. The method further includes refreshing the working surface of the SPR generation system by depositing a new layer of the first binding substance on the working surface of the SPR generation system.

The present technology also includes an illustrative apparatus for analyte monitoring using surface plasmons with a refreshable surface. The apparatus includes a first metal surface disposed over a glass surface, a light source that emits light through the glass surface and at the first metal surface, and a detection system that detects light reflected from the first metal surface. The apparatus further includes a chamber that contains a first binding substance for providing binding sites for an analyte to be monitored and a control system for controlling the apparatus. The control system is configured to cause a solution to be monitored to be placed in contact with the first metal surface and to cause the light source to emit light at the first metal surface at a plurality of angles over a period of time. The control system is also configured to cause the detection system to measure a reflectance of the light at each of the plurality of angles to determine an SPR angle and monitor changes to the SPR angle over the period of time and to determine that an amount of the analyte to be monitored within the solution to be monitored exceeds a predetermined threshold amount of the analyte to be monitored in response to detecting a rate of change of the SPR angle that decreases sooner than a predetermined threshold time. The control system is further configured to refresh the working surface of the SPR generation system by causing deposition of a new layer of the first binding substance on the working surface of the SPR generation system.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Various methods have been used to detect such pollutants. For example, surface-enhanced Raman spectroscopy (SERS) has been used and has proven to be an extremely sensitive method for performing quantitative and qualitative analyses of pollutants. A Raman spectrum, similar to an infrared spectrum, consists of a wavelength distribution of bands corresponding to molecular vibrations specific to the sample being analyzed (the analyte). According to Raman spectroscopy, a beam from a light source is focused upon the analyte to generate inelastically scattered radiation. This radiation is optically collected and directed into a wavelength-dispersive spectrometer in which a detector converts the energy of impinging photons to electrical signal intensity. The analyte can be analyzed and pollutants detected by the analysis of this electrical signal intensity.

Surface plasmon resonance (SPR) may also be used to detect pollutants. Such a system is configured so that a beam from a light source is focused through a glass substrate to a metal film adhered to the glass surface. The beam passes through the glass substrate and reaches the metal film at a high angle. When this angle is near a critical value (i.e., a resonance angle); light energy stimulates electron excitation (i.e., a surface plasmon) on the surface of the metal film. Changes in the optical properties near the metal surface cause this resonance angle to change. By monitoring the change of the resonance angle, adsorption of materials to the metal surface can be detected and quantified.

Described herein are illustrative methods and systems for monitoring analytes using surface plasmons with a refreshable surface. Such methods and systems allow for periodically providing clean surfaces for analyte adsorption and for the monitoring of such analytes.

Figure 1:
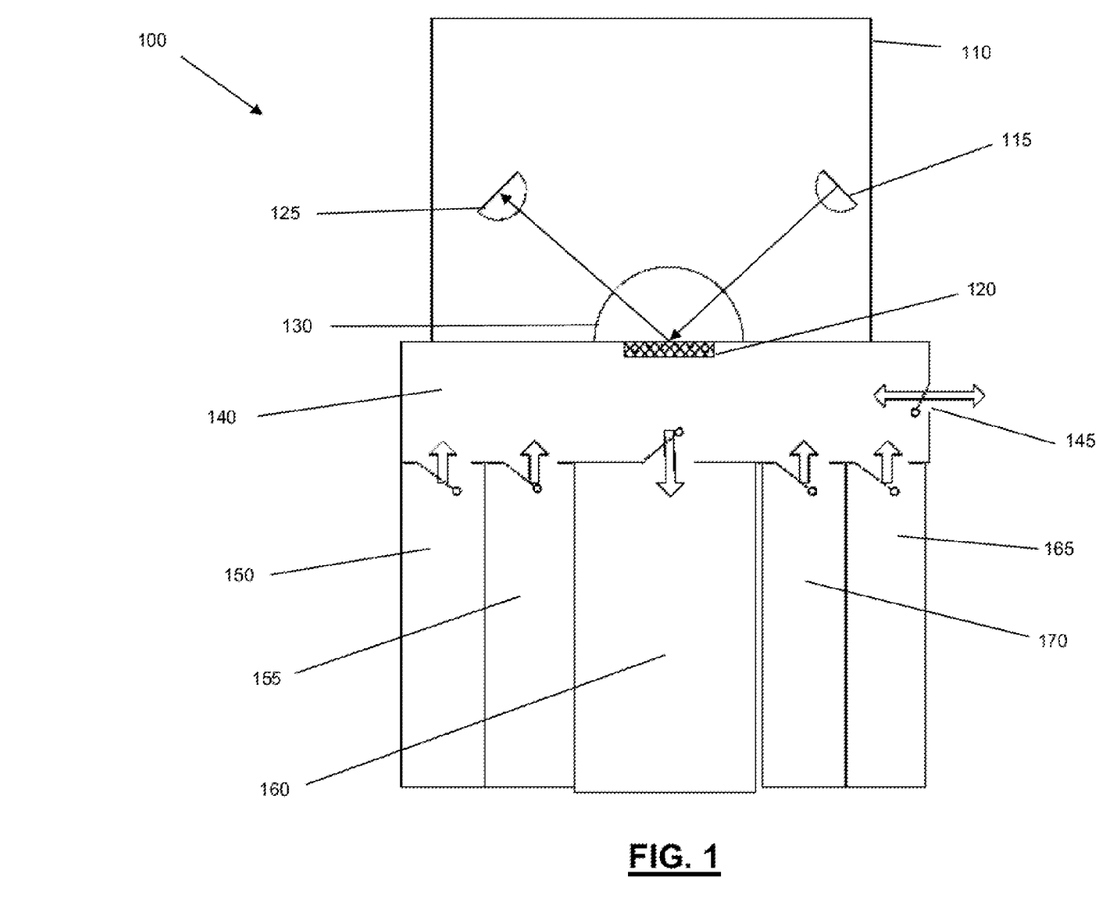
FIG. 1 depicts a surface plasmon resonance (SPR) measurement system in accordance with an illustrative embodiment.

FIG. 1 depicts a surface plasmon resonance (SPR) measurement system 100 in accordance with an illustrative embodiment. SPR measurement system 100 includes an optics and electronics chamber 110. In an embodiment, optics and electronics chamber 110 is an airtight chamber. Optics and electronics chamber 110 includes a light source 115, a light detection apparatus 125, and a glass substrate 130. In additional embodiments, glass substrate 130 may be substituted with any substrate which will allow for total internal reflection of emitted light at an interface between the substrate and a solution. A software or hardware control program is communicatively coupled to light source 115 and light detection apparatus 125 to control functioning of these devices.

In an embodiment, light source 115 is a laser light source such as a helium-neon laser or other suitable laser. Light source 115 may also comprise an incandescent light, a light emitting diode, a xenon lamp configured to emit a filtered, collimated light, or any other light source configured to emit a light that is substantially monochromatic and well-collimated. Light source 115 is configured to emit a beam of light through glass substrate 130 at a metal film 120. The emitted light may have any wavelength so long as metal film 120 is capable of support surface plasmon at such a wavelength. Metal film 120 is adhered to glass substrate 130 as is known to those of skill in the art. Accordingly, the beam of light passes through glass substrate 130 and reaches metal film 120 across a given range of angles. At least a portion of this beam of light is reflected from metal film 120 and is received at light detection apparatus 125.

When an angle at which the beam of light reaches metal film 120 is near a critical value (i.e., a resonance angle), light energy stimulates electron excitation, creating surface plasmons on the surface of metal film 120. The creation of the surface plasmons results from coupling that occurs between the plasma oscillations of free electrons in metal film 120 and the bound electromagnetic field produced by totally internal reflected photons. This coupling occurs as a result of the momentum of the incoming beam of light equaling the momentum of the bound electromagnetic field. The coupling causes photons from the beam of light produced by light source 115 to be converted to surface plasmons. Since these photons are not reflected, a "shadow" occurs in the reflected light at the resonance angle which can be detected by light detection apparatus 125.

Changes in the optical properties near the surface of metal film 120 causes the resonance angle to change. Light detection apparatus 125 is configured to monitor and detect any changes to the resonance angle. Changes to the resonance angle may result from the adsorption of materials to the surface of metal film 120 as discussed in more detail below.

In an embodiment, light detection apparatus 125 is a charge coupled device photoarray. In other embodiments, light detection apparatus 125 may include a photodiode sensor, a complementary metal-oxide-semiconductor sensor, or any other detection apparatus configured to allow simultaneous measurement of a light signal across a range of angles.

In an embodiment, optics and electronics chamber 110 may include a surface plasmon adsorbate monitor as described in an article by C. S. Mayo and R. B. Hallock entitled "Apparatus for the Study of Macromolecular Adsorption." (Mayo, CS, and Hallock, RB, "Apparatus for the Study of Macromolecular Adsoprtion," *Rev. Sci. Instrum.* 60 (1989)).

SPR measurement system 100 further includes an input chamber 140 that includes metal film 120 and that is configured to bring source water or any other substance or aqueous solution to be monitored into contact with metal film 120. Metal film 120 includes gold, silver, aluminum, copper or any other suitable metal for producing the SPR effects discussed throughout this specification. In an embodiment, an initial layer of metal film 120 adjacent to glass substrate 130 has a thickness between 30 and 80 nanometers and subsequent refreshed metal layers as discussed in more detail below may have a thickness between 1 and 200 nanometers. In an embodiment, the length and width of metal film 120 may range between 1 and 100 millimeters. Input chamber 140 also includes a first input/output valve 145 through which the source water may be pumped into and/or out of input chamber 140.

SPR measurement system 100 also includes a chamber 150 that includes a chemical compound A that is specific to the analyte/pollutant of interest. The chemical compound A is also capable of irreversibly binding to the metal surface of metal film 120, of providing irreversible binding sites for the analyte (i.e., binding sites that do not allow for a significant amount of desorption of the analyte upon a reduction in the concentration of the analyte within the solution), and of providing primarily weak and reversible binding sites for other materials that may be present in the source water or other substance or aqueous solution to be monitored. In an example embodiment, the analyte is arsenic and the chemical compound A is polyvinylpyrrolidone. In another embodiment, the analyte is pyrene, the chemical compound A is dithiocarbamate calix[4]arene, and the metal film is silver. In a third embodiment, the analyte is chrysene, the chemical compound A is humic acid, and the metal film is silver. In a fourth embodiment, the chemical compound A is an antigen, the analyte is an antibody for the antigen, and the metal film is gold.

The control program of SPR measurement system 100 is configured to cause the chemical compound A from chamber 150 to be placed into contact with metal film 120 within input chamber 140 for a sufficient time such that a layer of the chemical compound A binds with and is formed upon metal film 120. In an embodiment, the adsorption time may vary from 30 seconds for small molecules, to as long as ten hours for macromolecules such as polymers. After a layer of the chemical compound A has been sufficiently formed upon metal film 120, the excess, unbound chemical compound A may be pumped out of input chamber 140. The formation of a sufficiently well-formed layer may be determined by monitoring the adsorption rate of chemical compound A. As the adsorption rate becomes much less (e.g., by a factor of ten) than its initial rate when the solution was first introduced, the system has likely substantially completed the adsorption. In an embodiment, the excess chemical compound A may be pumped back into chamber 150. In an alternative embodiment, the excess chemical compound A may be pumped into a waste chamber 160.

SPR measurement system 100 may also include a clean water chamber 155. In an embodiment, clean water chamber 155 includes water that is substantially free of the analyte such that upon contact with metal film 120, the clean water will not cause a shift in the resonance angle. Alternatively, SPR measurement system 100 may not include clean water chamber 155 and instead input chamber 140 may simply be connected to a source of clean water.

Figure 2:
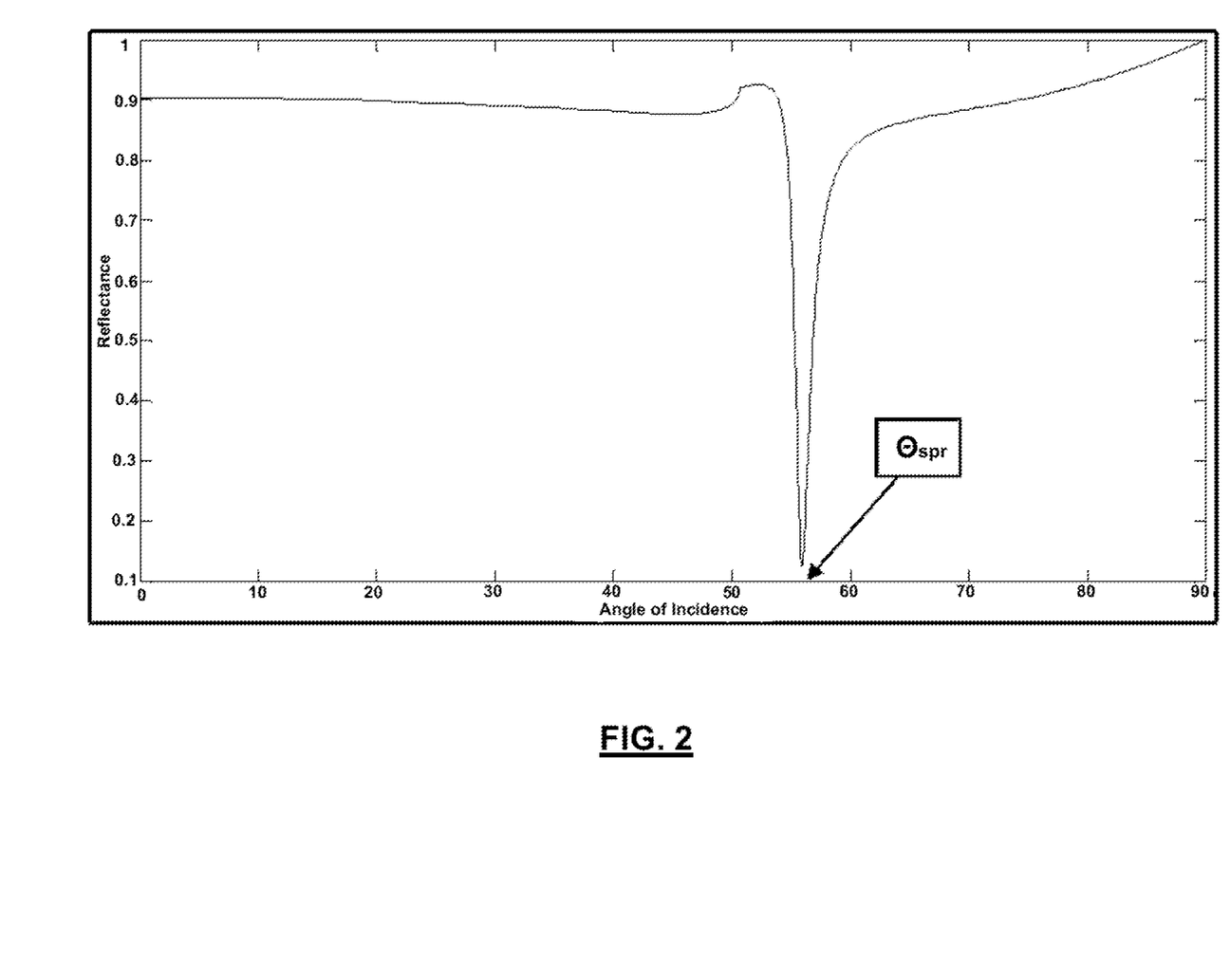
FIG. 2 depicts a reflectance curve measured by the SPR system in accordance with an illustrative embodiment.

The control program of SPR measurement system 100 is configured to cause the clean water to be moved into input chamber 140 and introduced to the metal film/chemical compound A surface of metal film 120. A control reflectance curve and resonance angle can then be measured using the components of optics and electronics chamber 110. FIG. 2 depicts a reflectance curve measured by the surface plasmon measurement system in accordance with an illustrative embodiment. The x-axis of the reflectance curve indicates the angle of incidence of the beam of light from light source 115 upon metal film 120. The y-axis of the reflectance curve indicates the fraction of light from light source 115 that is reflected from metal film 120 and detected at light detection apparatus 125. $\theta_{spr}$ indicates the resonance angle at which the fraction of light reflected is significantly reduced.

SPR measurement system 100 may also include a chamber 170 that includes a chemical compound B that is specific to the analyte/pollutant of interest. The chemical compound B that is specific to the analyte is also capable of irreversibly binding to the metal of metal film 120 and of providing binding sites for the analyte. In an embodiment, chemical compound B may be the same as chemical compound A or a different compound than chemical compound A. In an example embodiment, chemical compound B is polyvinylpyrrolidone. In another embodiment, chemical compounds A and B can be used to form a bilayer of an amphiphile (tail-to-head/head-to-tail) or a bilayer of two separate compounds. Such a configuration allows one side of the bilayer to bind to metal film 120, while the other side of the bilayer provides binding sites for the analyte and promotes the irreversible binding of the analyte or metal to the bilayer. A bilayer helps avoid binding at both ends of a single chemical compound A or B, which may inhibit analyte adsorption. In additional embodiments, SPR measurement system 100 may include additional chambers for storage of additional compounds used to form bilayers or to provide additional binding sites.

In another embodiment, chamber 170 may be omitted from SPR measurement system 100 and chemical compound A and chamber 150 may be used in place of chemical compound B and chamber 170.

The control program of SPR measurement system 100 is configured to cause the chemical compound B from chamber 170 to be placed into contact with the analyte/chemical compound A/metal surface of metal film 120 within input chamber 140 for a sufficient time such that a layer of the chemical compound B binds with and is formed upon the exposed analyte/chemical compound A/metal surface of metal film 120. The time required for binding of chemical compound B with the surface may vary from a few seconds to several hours. In an embodiment, smaller molecules may be used to keep the layer of chemical compound B thin and to reduce the adsorption time. Other variables that may affect the adsorption time include the concentration of chemical compound B, the diffusion rate of chemical compound B, the binding strength of the analyte to chemical compound B, the temperature of the system, the pH of the system, and the cleanliness of the analyte surface. Factors such as higher concentration, faster diffusion rate, higher binding strength, higher temperature, appropriate pH, and greater cleanliness may decrease the adsorption time.

After a layer of chemical compound B has been sufficiently formed upon the analyte/chemical compound A/metal surface, the excess, unbound chemical compound B is pumped out of input chamber 140. In an embodiment, the excess chemical compound B may be pumped back into chamber 170. In an alternative embodiment, the excess chemical compound B may be pumped into waste chamber 160.

SPR measurement system 100 can also include a metal chamber 165 that includes a metal in colloidal form. In an embodiment, the metal stored in metal chamber 165 is the same metal as that of metal film 120. In an alternative embodiment, the metal stored in metal chamber 165 may be a different metal than that of metal film 120 so long as the metal of metal chamber 165 is capable of irreversibly binding with the desired analyte. The metal stored in metal chamber 165 may include gold, silver, aluminum, copper or any other suitable metal for producing the SPR effects discussed throughout this specification.

The control program of SPR measurement system 100 is configured to cause the metal from metal chamber 165 to be placed into contact with the chemical compound B on the surface of metal film 120 within input chamber 140 for a sufficient time such that a layer of the metal binds with the layer of the chemical compound B on the surface of metal film 120. The time required for binding of the metal with chemical compound B may vary from a few seconds to several hours. In an embodiment, smaller molecules may be used to keep the layer of metal thin and to reduce the adsorption time. Other variables that may affect the adsorption time include the concentration of the metal, the diffusion rate of the metal, the binding strength of the metal to chemical compound B, the temperature of the system, the pH of the system, and the cleanliness of the surface. A higher concentration, diffusion rate, binding strength, temperature, and pH and greater cleanliness will decrease the adsorption time.

After a layer of the metal has sufficiently bound to the layer of chemical compound B on the surface of metal film 120, the excess unbound metal is pumped out of input chamber 140. In an embodiment, the excess metal may be pumped back into chamber 165. In an alternative embodiment, the excess metal may be pumped into waste chamber 160.

Figure 3:
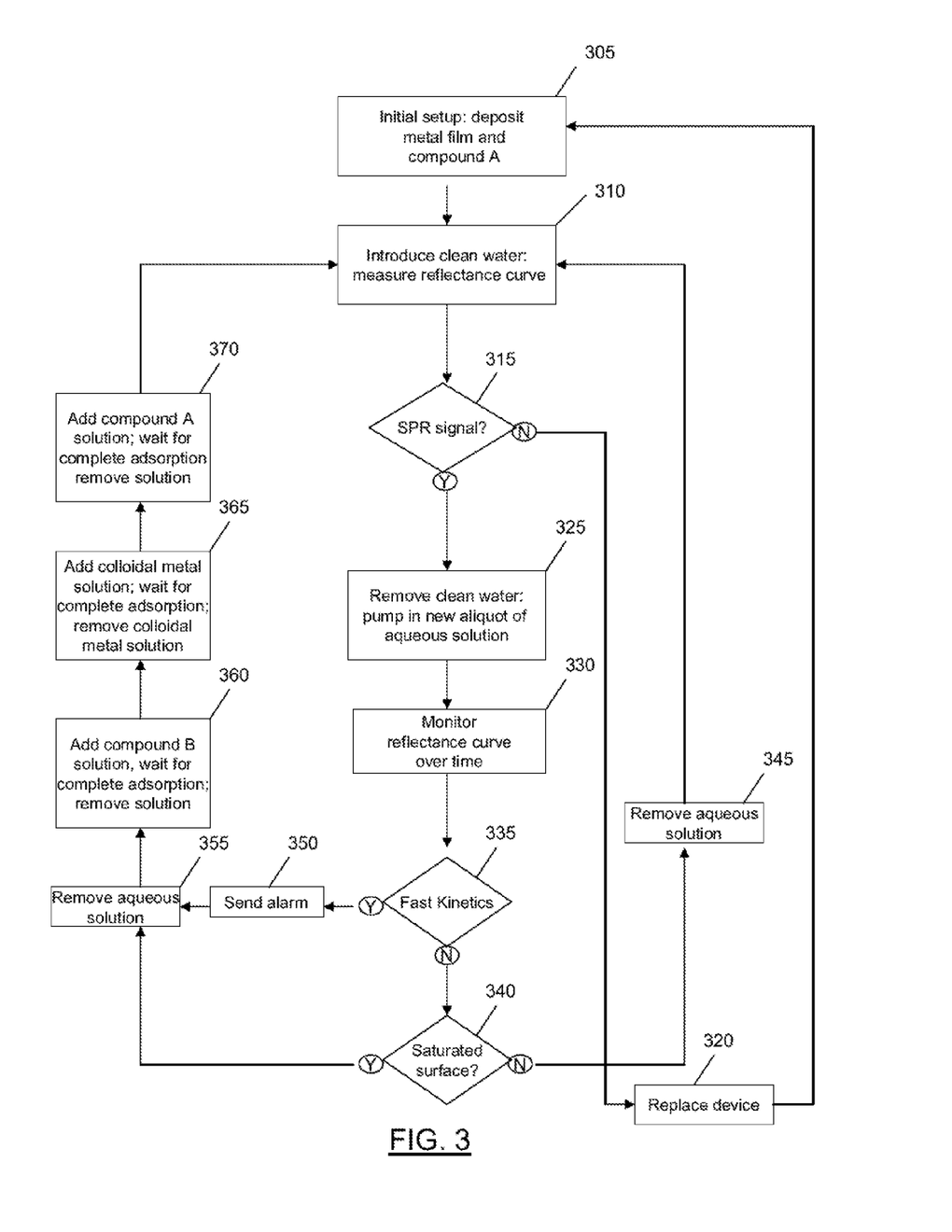
FIG. 3 depicts a method of analyte monitoring using surface plasmons with a refreshable surface in accordance with an illustrative embodiment.

FIG. 3 depicts a method of analyte monitoring using surface plasmons with a refreshable surface in accordance with an illustrative embodiment. In an operation 300, a chemical compound A that is specific to an analyte to be monitored is deposited on a surface of a metal film of an SPR measurement system similar to SPR measurement system 100 of FIG. 1. According to an embodiment, chemical compound A is able to irreversibly bind to the surface of the metal film, to provide irreversible binding sites for the analyte, and to provide primarily weak and reversible binding sites for other materials that may be present in a source water or other aqueous solution to be monitored. In an example embodiment, the analyte is arsenic and the chemical compound A is polyvinylpyrrolidone. In another embodiment, the analyte is pyrene, the chemical compound A is dithiocarbamate calix[4]arene, and the metal film is silver. In a third embodiment, the analyte is chrysene, the chemical compound A is humic acid, and the metal film is silver. In a fourth embodiment, the chemical compound A is an antigen, the analyte is an antibody for the antigen, and the metal film is gold.

In an operation 310, clean water that is substantially free of the analyte is introduced to the SPR measurement system so that the clean water is placed in contact with the chemical compound A/metal surface of the metal film and a reflectance curve is measured by the SPR measurement system. In an embodiment, the reflectance curve is determined by emitting a beam of light at an interface between the metal film and a glass substrate which is in turn reflected from the interface and detected at a light detection apparatus. The incident angle of the beam of light upon the interface is varied across a range of angles and the magnitude of the reflection is detected by the light detection apparatus and associated with the corresponding incident angle. The resonance angle is determined as the incident angle at which the fraction of light reflected and received at the light detection apparatus is substantially less than other incident angles (as illustrated in FIG. 2).

In an operation 315, it is determined whether or not an SPR signal exists (e.g., whether a resonance angle is detected). If an SPR signal does not exist, the SPR measurement system is determined to be defective and the system may be replaced in an operation 320. If an SPR signal does exist, the clean water is removed and a new aliquot of an aqueous solution to be monitored is introduced to the chemical compound A/metal surface of the metal film in an operation 325. In an operation 330, the reflectance curve produced by a light source reflected from the metal film when the chemical compound A/metal surface of the metal film is in contact with the new aliquot of aqueous solution is monitored over time.

In an operation 335, the SPR resonance angle and/or its rate of change are monitored. A change, Y, in the SPR resonance angle, and its rate of change, $\Delta Y/\Delta t$, can typically be described as a function of time, t, and adsorbate concentration, C, using the following functions:

$$Y=Y_o[1-\exp(-kCt)](k>0) \quad \text{(eq. 1)}$$

$$\Delta Y/\Delta t=kCY_o\exp(-kCt) \quad \text{(eq. 2)}$$

$$t_C=3/kC \quad \text{(eq. 3)}$$

Initially, at a time t=0, the shift of the SPR resonance angle is zero. At t>0, the rate of change of the SPR resonance angle is large at first, but then decreases until it approaches zero as the available binding sites for the analyte are used up. The total angular change reaches about 95 percent of its final value when $t=t_C$, as indicated by equation 3. At this time, the rate of angular change is about 5 percent of its initial rate. Please note that in additional embodiments, percentages other than 95 percent/5 percent may be used according to the design needs of the system, analyte, solution, etc. By monitoring the shift of the SPR resonance angle and its rate of change, the final SPR resonance angle can be inferred. In addition, the rate of change of the SPR resonance angle is indicative of the concentration of the adsorbate, C.

As the adsorption of the analyte proceeds, the SPR resonance angle asymptotically approaches its final value. The asymptotic stage of the adsorption can be estimated as the time when the rate of change of the SPR resonance angle has decreased to a predetermined percentage of the initial rate of change. In an embodiment, this predetermined percentage of the initial rate of change may be less than 5 percent of its initial rate of change. At this time, the angular shift is 95 percent of its final value, i.e., $Y=0.95Y_o$. In alternative embodiments, the predetermined percentage of the initial rate of change may be other percentages based on the particular design needs of the system.

In operation 335, the system is determined to exhibit "fast kinetics" when the time required for the rate of change of the SPR resonance angle to reach the predetermined percentage of its initial rate of change (e.g., 5 percent of its initial rate of change) is sufficiently small that it does not exceed a predetermined threshold time. In an embodiment, the fast kinetics situation is independent of the total change in the resonance angle and is dependent solely on the analyte concentration C and the adsorption constant k of the analyte, as described in equations 1 and 2. In an embodiment, the predetermined threshold time may be previously determined by measuring changes to the SPR resonance angle in response to introduction of a control solution, e.g., a solution having a predetermined threshold amount of the analyte. For example, if the threshold level for an unacceptably high concentration of the analyte is 100 parts per billion (ppb), then the adsorption rate can be pre-determined (in an analytical lab, for example) using such a solution (i.e., a solution having 100 ppb of the analyte). If in this example, it takes 30 seconds for a 100 ppb solution to reach its asymptotic adsorption value (i.e., the point at which the rate of change of the SPR resonance angle has reached the predetermined percentage of its initial rate of change (e.g., 5 percent of its initial value)), then a detected time for a tested solution to reach the predetermined percentage of its initial rate of change that is less than 30 seconds will cause a determination that the adsorption process is exhibiting fast kinetics.

If the time required for the rate of change of the SPR resonance angle to reach the predetermined percentage of its initial rate of change is less than the predetermined threshold time, it is determined that an amount of the analyte within the aqueous solution exceeds a predetermined threshold amount of the analyte in an operation 350. Optionally, a notification may be triggered. The notification may include an alarm, a light, a text message, an email, or any other notification known to those of skill in the art.

If fast kinetics are not exhibited, a determination is made as to whether the chemical compound A/metal surface of the metal film had sufficient available binding sites for the analyte prior to introduction of the solution in an operation 340. If the total change of the reflectance curve and/or the SPR resonance angle is greater than a predetermined total change expected for a solution containing the analyte, a determination is made that the chemical compound A/metal surface of the metal film had a sufficient, quantity of available binding sites in an operation 340, and the aliquot of aqueous solution is removed from contact with the chemical compound A/metal surface of the metal film in an operation 345. The method may then return to operation 310. In an example embodiment, if the total change is greater than 80 percent of the total expected change, the determination may be made that the chemical compound A/metal surface of the metal film is not saturated. In alternative embodiments, any percentage of the total expected change may be used as the threshold for the determination that the chemical compound A/metal surface of the metal film is not saturated/has available binding sites in accordance with the design needs of the particular system.

If the total change of the reflectance curve and/or the SPR resonance angle is small, and the time for the reflectance curve and/or the SPR resonance angle to reach the predetermined percentage of its initial rate of change (e.g., 5 percent of its initial rate of change or any other selected percentage based on the design needs of the system) exceeds the predetermined time limit, a determination is made that the chemical compound A/metal surface of the metal film did not have a sufficient quantity of available binding sites in operation 340. In an embodiment, the total change of the reflectance curve and/or the SPR resonance angle may be considered small if the total change is less than 80 percent of the total expected change in the reflectance curve and/or the SPR resonance angle. In alternative embodiments, any percentage of the total expected change may be used as the threshold for the determination that the chemical compound A/metal surface of the metal film is saturated/lacks sufficient available binding sites in accordance with the design needs of the particular system so long as this percentage does not exceed the percentage used for the determination that the chemical compound A/metal surface of the metal film is not saturated.

In an operation 355, the aliquot of aqueous solution is removed from contact with the chemical compound A/metal surface of the metal film. In an operation 360, a chemical compound B is deposited on the analyte-saturated surface of the metal film. In an embodiment, a solution comprising chemical compound B is moved into a chamber that includes the analyte-saturated surface of the metal film and the chemical compound B adsorbs to the analyte-saturated surface of the metal film. After the chemical compound B has been sufficiently deposited on the analyte-saturated surface of the metal film such that a layer of the chemical compound B is disposed over the surface, the chemical compound B solution is removed from the chamber. As discussed above, depending on numerous variables the time required for sufficient adsorption of chemical compound B to the analyte-saturated surface of the metal film may vary from a few seconds to several hours. In an embodiment, deposition/adsorption of chemical compound B is sufficient when approximately 80% of the analyte-saturated surface of the metal film is covered with chemical compound B. In an embodiment, the thickness of the adsorbed/deposited layer of chemical compound B less than 4 nanometers although greater thicknesses are possible, and the deposition is determined to be sufficient when the rate of adsorption of chemical compound B has dropped to 5 percent of its initial rate of adsorption.

In an embodiment, chemical compound B is specific to the analyte/pollutant of interest and is capable of irreversibly binding to the analyte/pollutant of interest and to the metal of the metal film. Chemical compound B may be the same as chemical compound A. In an example embodiment, chemical compound B is polyvinylpyrrolidone. In another embodiment, chemical compound B is used to form a bilayer of an amphiphile or a bilayer of two separate compounds.

In an operation 365, a colloidal metal is deposited on the surface of the metal film after deposition of the chemical compound B on the surface of the metal film. In an embodiment, a solution comprising the colloidal metal is moved into the chamber that includes the surface of the metal film and the colloidal metal adsorbs to the chemical compound B previously deposited on the surface of the metal film. After the colloidal metal has been sufficiently deposited on the surface of the metal film such that a layer of the colloidal metal is formed over the surface, the colloidal metal solution is removed from the chamber. The time required for sufficient deposition/adsorption of the colloidal metal to layer of chemical compound B may vary from few seconds to several minutes. In an embodiment, deposition/adsorption of the colloidal metal is sufficient when approximately 80 percent of the layer of chemical compound B is covered with the colloidal metal. In an embodiment, the layer of chemical compound B will be approximately completely covered with the colloidal metal such that the layer of colloidal metal has a thickness of between 1 and 100 nm.

In an embodiment, the colloidal metal is capable of irreversibly binding to the chemical compound B. In an example embodiment, the colloidal metal may include gold, silver, aluminum, copper or any other suitable metal for producing the SPR effects discussed throughout this specification.

In an operation 370, a chemical compound A is deposited on the surface of the metal film. In an embodiment, a solution comprising chemical compound A is moved into a chamber that includes the surface of the metal film and the chemical compound A adsorbs to the previously deposited colloidal metal on the surface of the metal film. After the chemical compound A has been sufficiently deposited on the surface of the layer of colloidal metal, the chemical compound A solution is removed from the chamber, and the method may return to operation 310. As discussed above, depending on numerous variables the time required for sufficient adsorption of chemical compound A to the layer of colloidal metal on the surface of the metal film may vary from a few seconds to several hours. In an embodiment, deposition/adsorption of chemical compound A is sufficient when approximately 80 percent of the surface of the layer of colloidal metal is covered with chemical compound A. In an embodiment, the thickness of the adsorbed/deposited layer of chemical compound A less than 4 nanometers although greater thicknesses are possible, and the deposition is determined to be sufficient when the rate of adsorption of chemical compound A has dropped to 5 percent of its initial rate of adsorption.

In an embodiment, chemical compound A is specific to the analyte/pollutant of interest and is capable of irreversibly binding to the analyte and to the previously deposited colloidal metal. Chemical compound A may be the same as chemical compound B. In an example embodiment, chemical compound A is polyvinylpyrrolidone. In alternative embodiments, chemical compound A may include dithiocarbamate calix[4]arene, humic acid, proteins, antibodies, antigens, or any other substance known to those of skill in the art capable of irreversibly binding to the analyte and to the previously deposited colloidal metal.

Figure 4:
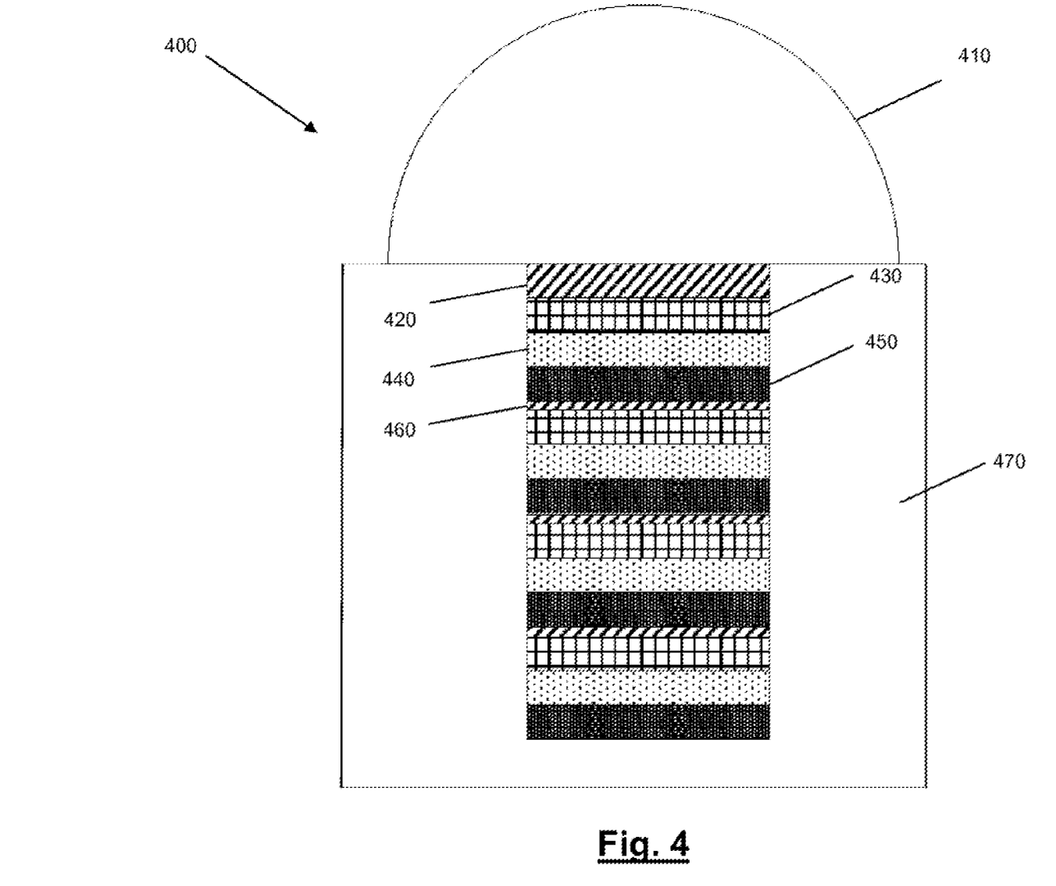
FIG. 4 depicts an SPR structure including a plurality of layers deposited on a metal film of an SPR measurement system accordance with an illustrative embodiment.

FIG. 4 depicts an SPR structure 400 that includes a plurality of layers deposited on a metal film of an SPR measurement system in accordance with an illustrative embodiment. SPR structure 400 includes a glass substrate 410, a metal film 420 adjacent to glass substrate 410, and an aqueous solution 470 in contact with metal film 420. In an embodiment, metal film 420 has a depth of approximately 50 nanometers (nm). In another embodiment, metal film 420 may have a thickness between 30 and 80 nanometers, and a length and width between 1 and 100 millimeters.

In the embodiment of FIG. 4, the surface of metal film 420 has been refreshed three times. This is merely an example embodiment, and the surface of metal film 420 may be refreshed fewer or more times in accordance with the specific operating needs of the associated SPR measurement system.

A layer 430 of chemical compound A is deposited upon a surface of metal film 420. In an embodiment, layer 430 of chemical compound A has a depth of between approximately 1 and 10 nm. In another embodiment, layer 430 of chemical compound A may have a depth of up to 40 nm. A layer 440 of an analyte is deposited upon a surface of layer 430 of chemical compound A. In an embodiment, layer 440 of the analyte has a depth of between approximately 1 and 10 nm. A layer 450 of chemical compound B is deposited on layer 440 of the analyte. In an embodiment, layer 450 of chemical compound B has a depth of between approximately 1 and 10 nm. A layer 460 of colloidal metal is deposited on layer 440 of chemical compound B. In an embodiment, layer 460 of colloidal metal has a depth of approximately 1 nm. In other embodiments, the layer of colloidal metal may have a depth between 1 and 200 nanometers.

Figure 5:
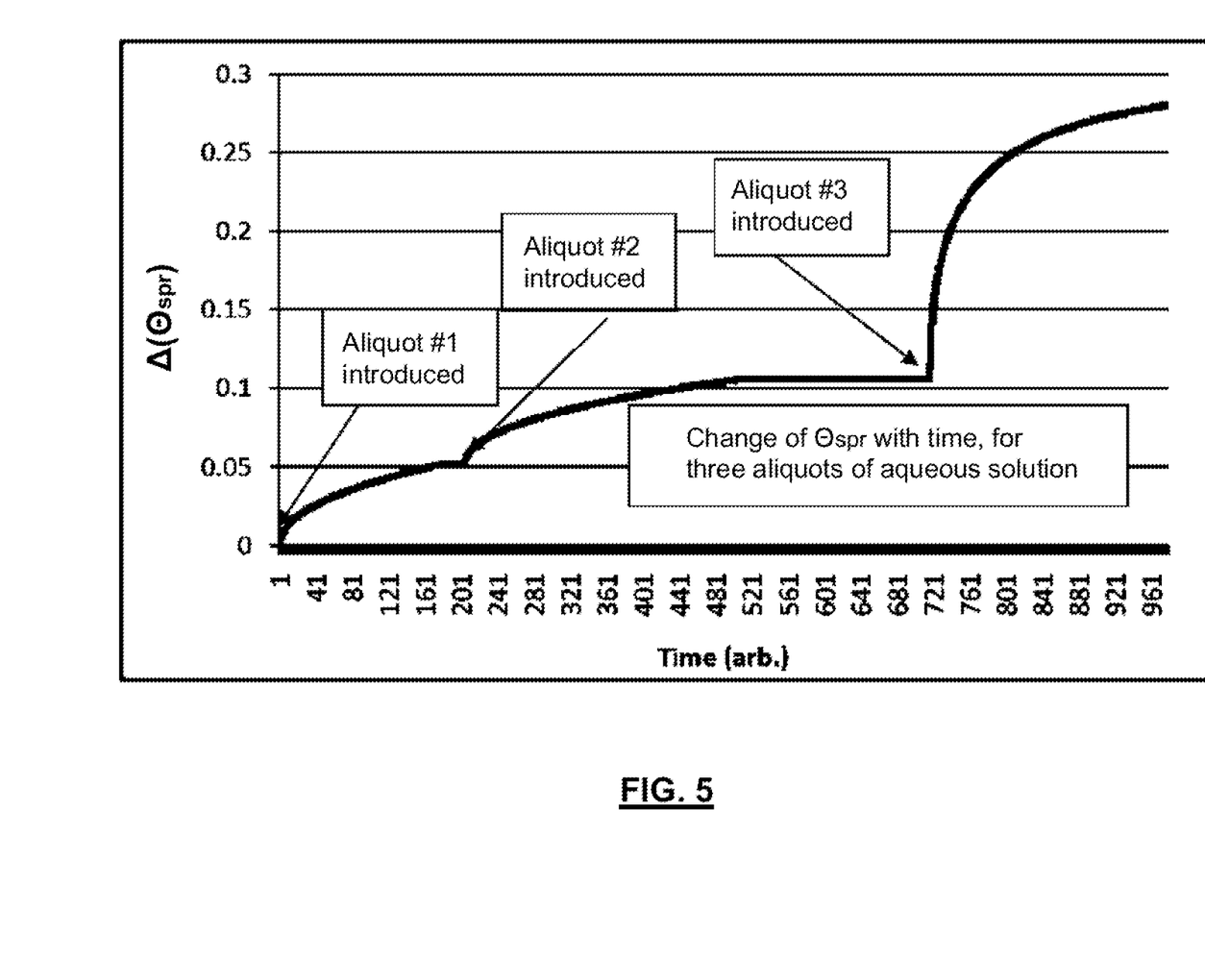
FIG. 5 depicts a graph illustrating the total change of a resonance angle over time in accordance with an illustrative embodiment.
Figure 6:
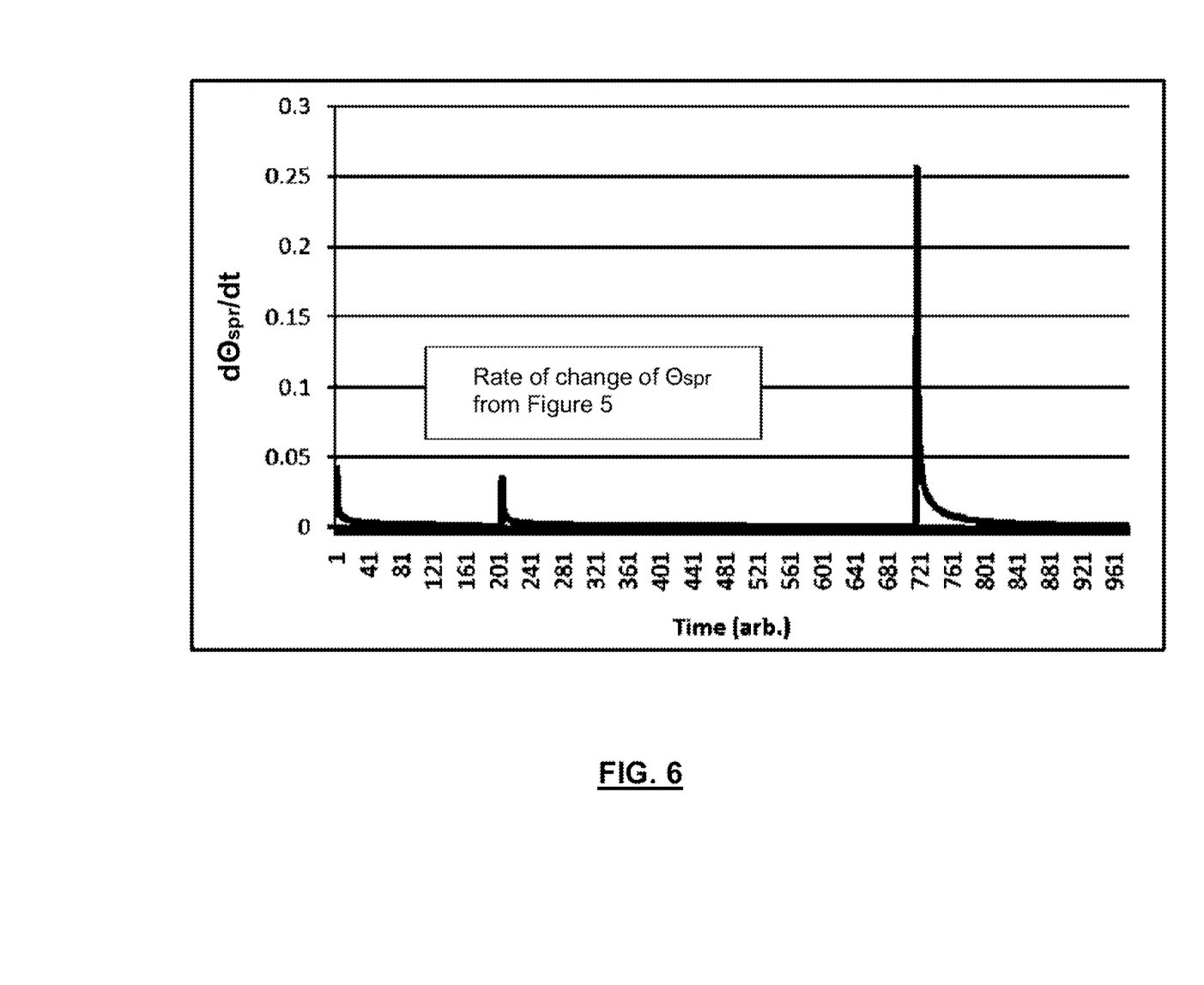
FIG. 6 depicts a graph illustrating the rate of change of a resonance angle over time in accordance with an illustrative embodiment.

FIG. 5 depicts a graph illustrating the total change of a resonance angle over time in accordance with an illustrative embodiment. FIG. 6 depicts a graph illustrating the rate of change of a resonance angle over time in accordance with an illustrative embodiment. In the embodiment illustrated in FIGS. 5 and 6, the change of the resonance angle is measured over time in response to three aliquots of aqueous solution being introduced to an SPR measurement system. The introduction of the first and second aliquots results in a relatively small and gradual change in the resonance angle. For example, the introduction of the first aliquot results in a change in the resonance angle of about 0.05 degrees over about 200 seconds, and the introduction of the second aliquot results in a change in the resonance angle of about 0.05 degrees over about 500 seconds. For both aliquots, the adsorption rate slows to about 5 percent of the initial adsorption rate after about 158 seconds following introduction of each aliquot.

In contrast, the introduction of the third aliquot results in a relatively large and rapid change in the resonance angle. For example, the introduction of the third aliquot results in a change in the resonance angle of about 0.15 degrees over about 80 seconds. The adsorption rate slows to about 5 percent of the initial rate after only 54 seconds following introduction of the aliquot, which is almost three times faster than for the two previous aliquots. The relatively rapid attainment of the reduced rate of change in the resonance angle in response to introduction of the third aliquot indicates that a much larger quantity of the analyte is present in the third aliquot than in the first or second aliquots.

EXAMPLES

Example 1

An SPR measurement system 100 including a metal film of silver, a chemical compound a of polyvinylpyrrolidone, and an analyte of arsenic in aqueous solution.

According to such an embodiment, light source 115 is a helium-neon laser that emits a light having a wavelength of 633 nm, glass substrate 130 is an SF10 glass with an index of refraction of 1.72, and metal film 120 is silver with an index of refraction of −0.059+4.2313i and an initial thickness of 50 nanometers. Clean water having an index of refraction of 1.33 is placed into contact with metal film 120 and an SPR angle is measured and found to be 54.66°. After removing the clean water, a solution of 3 parts per billion (ppb) of chemical compound A in water is introduced to the metal film surface so that the chemical compound A will adsorb to the surface of the metal film. According to this embodiment, the chemical compound A is polyvinylpyrrolidone (PVP). The SPR angle is again measured. After 30 minutes, the SPR angle has stabilized at 54.86°, an increase of 0.4°. The chemical compound A/PVP solution is removed and replaced with clean water. The SPR angle remains at 54.86°. An aqueous test solution is introduced and tested for arsenic. In this instance, the aqueous test solution contains arsenic at a very low concentration (less than 10 ppb). The SPR angle increases by 0.01° in the first hour. The small increase in the SPR angle does not trigger a notification, as the adsorption rate of the SPR angle is below the notification threshold of 0.3 degrees in thirty minutes.

The aqueous test solution is then removed and the chemical compound A/PVP solution is introduced a second time. After 30 minutes, the chemical compound A/PVP solution has caused the SPR angle to increase to 55.07°, which indicates a PVP layer thickness of 1.7 nm. The chemical compound A/PVP solution is then removed and replaced with a solution of colloidal silver, which lowers the SPR angle to 54.95° after 10 minutes. This change in the SPR angle corresponds to a silver layer thickness of 2 nm. The solution of colloidal silver is then removed, and the chemical compound A/PVP solution is re-introduced and allowed to adsorb for 30 minutes, causing the SPR angle to increase to 55.15°. The SPR angle change corresponds to the deposition/adsorption of a layer of PVP approximately 1.7 nm thick.

A new aqueous test solution is introduced, this time containing 100 ppb of arsenic. The SPR angle increases by 0.02° in the first two minutes. After one hour, the SPR angle has stabilized at 55.23°. The initial rate of change (0.60° per hour) is above the notification threshold of 0.3 degrees in thirty minutes, causing a notification to be triggered.

The chemical compound A/PVP solution is once again introduced and the cycle is repeated, with SPR angle increases ranging between 0.28° and 0.37°, depending on the amount of arsenic present in the test solution. After 20 iterations, the SPR angle has reached 61.63°, but the depth of the minimum reflected signal has become quite weak. On the $21^{st}$ iteration, the minimum reflected signal can no longer be detected, indicating that the electric field can no longer penetrate through the 21 refreshed layers to the current surface. At this point, the chemical compound A/PVP solution is removed, and a notification is sent indicating that the unit needs to be replaced.

Example 2

An SPR measurement system 100 including a metal film of gold, a chemical compound a of bovine serum albumin (BSA), and an analyte of bovine IgG immunoglobulin.

According to such an embodiment, light source 115 is a helium-neon laser that emits light having a wavelength of 633 nm, glass substrate 130 is an SF10 glass with an index of refraction of 1.72, and metal film 120 is gold with an index of refraction of −0.227+3.31i and an initial thickness of 50 nanometers. Clean water having an index of refraction of 1.33 is placed into contact with metal film 120 and an SPR angle is measured and found to be 57.75°. After removing the clean water, a saline solution containing 3 parts per billion (ppb) of chemical compound A in water is introduced to the metal film surface so that the chemical compound A will adsorb to the surface of the metal film. According to this embodiment, the chemical compound A is BSA.

The SPR angle is again measured. After 90 minutes, the SPR angle has stabilized at 58.93°, an increase of 1.18° from the initial measurement of 57.75°. The BSA solution is removed and replaced with clean water. The SPR angle remains at 58.93°. An aqueous test solution of bovine IgG immunoglobulin is introduced and tested for rabbit anti-bovine serum albumin (RABSA). In this instance, the aqueous test solution contains no RABSA, so that the SPR angle does not change over the course of five hours.

The aqueous test solution is then removed and a solution that contains 10 ppb of RABSA is introduced. After 90 minutes, the RABSA solution has caused the SPR angle to increase to 59.94°, which indicates a RABSA layer thickness of 1.0 nm. This increase is greater than the notification threshold of 0.4 degrees over 90 minutes; hence a notification is triggered. The RABSA solution is then removed and replaced with a solution of colloidal gold, which lowers the SPR angle to 59.42° after 10 minutes. This change in the SPR angle corresponds to a gold layer thickness of 2.0 nm. The solution of colloidal gold is then removed, and the BSA solution is re-introduced and allowed to adsorb for 90 minutes, causing the SPR angle to increase to 60.66°. The SPR angle change corresponds to the deposition/adsorption of a layer of BSA approximately 6.0 nm thick.

A new aqueous test solution is introduced, this time containing 1 ppb of RABSA, which is below the alarm level of 2 ppb. The SPR angle increases by 0.2° in the first 90 minutes, which is below the notification threshold of 0.4 degrees in 90 minutes.

The chemical BSA solution is once again introduced and the cycle is repeated, with SPR angle increases ranging between 0.2° and 1.2°, depending on the amount of RABSA present in the test solution. After ten iterations, the SPR angle has reached 72.75°, but the depth of the minimum reflected signal has become quite weak. On the eleventh iteration, the minimum reflected signal can no longer be detected, indicating that the electric field can no longer penetrate through the eleven refreshed layers to the current surface. At this point, the BSA solution is removed, and a notification is sent indicating that the unit needs to be replaced.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method for detecting at least one analyte, the method comprising:
   providing a solution to be monitored for the at least one analyte;
   placing the solution to be monitored in contact with a working surface of a surface plasmon resonance (SPR) generation system, wherein the working surface comprises a first metal surface disposed on a glass surface, and wherein the first metal surface comprises a first binding substance configured to provide binding sites for the analyte;
   applying light to the first metal surface at a plurality of angles over a period of time;
   measuring a reflectance of the light at each of the plurality of angles to determine an SPR angle;

monitoring changes to the SPR angle over the period of time to determine if an amount of the analyte within the solution to be monitored exceeds a predetermined threshold amount of the analyte, wherein the amount of the analyte within the solution to be monitored exceeds the predetermined threshold amount of the analyte if a detected decrease in a rate of change of the SPR angle occurs sooner than a predetermined threshold time; and refreshing the working surface of the SPR generation system by depositing a new layer of the first binding substance on the working surface of the SPR generation system, wherein the refreshing the working surface comprises:

removing the solution to be monitored from contact with the working surface:

depositing a second binding substance over the working surface, wherein the second binding substance is configured to irreversibly bind to the analyte that has bound to the working surface;

depositing a second metal surface over the second binding substance; and depositing the first binding substance over the second metal surface.

2. The method of claim 1, further comprising:
placing a control solution in contact with the working surface of the SPR generation system;
determining whether a shape of a reflectance curve indicates the presence of SPR at the working surface, wherein the reflectance curve is generated by applying light to the first metal surface while the first metal surface is in contact with the control solution; and
performing the placing the solution to be monitored in contact with the working surface after determining that the shape of the reflectance curve is compatible with the presence of SPR at the working surface.

3. The method of claim 1, further comprising issuing a notification in response to detecting the decrease in the rate of change of the SPR angle that occurs sooner than the predetermined threshold time, wherein the predetermined threshold time is determined based on an expected decrease in a rate of change of an SPR angle for a control solution.

4. The method of claim 1, further comprising depositing the first binding substance over the first metal surface, wherein the depositing the first binding substance over the first metal surface comprises placing the first metal surface in contact with a solution that includes the first binding substance.

5. The method of claim 1, further comprising generating a reflectance curve by measuring the reflectance of the light at each of the plurality of angles over the period of time, and determining an SPR reflectance minimum angle from the reflectance curve.

6. The method of claim 1, wherein the rate of change of the SPR angle corresponds to a rate of change of adsorption of the analyte to the first binding substance.

7. The method of claim 1, wherein the refreshing the working surface of the SPR generation system is performed in response to a rate of decrease in the rate of change of the SPR angle decreasing to below a second predetermined threshold rate of decrease in the rate of change.

8. The method of claim 1, wherein the depositing a second binding substance comprises introducing a second solution to the working surface, wherein the second solution includes the second binding substance, and wherein the depositing a second metal surface comprises depositing a colloid of metal nanoparticles over the second binding substance.

9. The method of claim 1, wherein at least one of the first binding substance and the second binding substance comprise polyvinylpyrrolidone.

10. A method for refreshing a working surface of a surface plasmon resonance (SPR) generation system, the method comprising:

removing a solution to be monitored from contact with a working surface of the SPR generation system, wherein the working surface comprises a first metal surface disposed on a glass surface, wherein the first metal surface comprises a first binding substance configured to provide binding sites for an analyte, wherein the SPR generation system further comprises a light source configured to apply light to the first metal surface at a plurality of angles over a period of time, and a detector configured to measure a reflectance of the light at each of the plurality of angles to determine an SPR angle;

depositing a second binding substance on the working surface, wherein the second binding substance is configured to irreversibly bind to the analyte that has bound to the working surface;

depositing a second metal surface over the second binding substance; and depositing the first binding substance on the second metal surface.

11. The method of claim 10, wherein the first metal surface is in a first chamber, and wherein the glass surface is enclosed in a second chamber that is airtight.

12. The method of claim 10, wherein the first metal surface comprises at least one of gold, silver, aluminum, or copper, and wherein the first binding substance comprises polyvinylpyrrolidone.

13. The method of claim 10, wherein the first binding substance comprises polyvinylpyrrolidone.

14. The method of claim 10, further comprising:
applying the light to the first metal surface at a plurality of angles over a period of time;
measuring the reflectance of the light at each of the plurality of angles to determine the SPR angle; and
monitoring changes to the SPR angle over the period of time to determine if an amount of the analyte within the solution to be monitored exceeds a predetermined threshold amount of the analyte, wherein the amount of the analyte within the solution to be monitored exceeds the predetermined threshold amount of the analyte if a detected decrease in a rate of change of the SPR angle occurs sooner than a predetermined threshold time.

15. An apparatus comprising:
a working surface comprising a first metal surface disposed over a glass surface;
a light source configured to emit light through the glass surface and at the first metal surface;
a detection system configured to detect light reflected from the first metal surface;
a chamber configured to contain a first binding substance configured to provide binding sites for at least one analyte to be monitored, wherein the chamber is in fluid communication with the working surface; and
a control system configured to:
cause a solution to be monitored to be placed in contact with the first metal surface;
cause the light source to emit light at the first metal surface at a plurality of angles over a period of time;
cause the detection system to measure a reflectance of the light at each of the plurality of angles to determine an SPR angle and monitor changes to the SPR angle over the period of time; and determine that an amount of the analyte to be monitored within the solution to be monitored exceeds a predetermined threshold amount of the analyte to be monitored in response to detecting a rate of change of the SPR angle that decreases sooner than a predetermined threshold time; and refresh the working surface, wherein to refresh the working surface the control system is further configured to:
 cause the solution to be monitored to be removed from contact with the first metal surface;
 cause a second binding substance to be deposited over the first metal surface and the analyte, wherein the second binding substance is configured to irreversibly bind to the analyte to be monitored that has previously bound to the first metal surface;
 cause a second metal surface to be deposited over the second binding substance; and
 cause the first binding substance to be deposited over the second metal surface.

16. The apparatus of claim 15, wherein the first metal surface is in a first chamber, wherein the glass surface is enclosed in a second chamber that is airtight, wherein the first metal surface comprises at least one of gold, silver, aluminum, or copper, and wherein the first binding substance comprises polyvinylpyrrolidone.

17. The apparatus of claim 15, wherein the control system is further configured to issue a notification in response to detection of the rate of change of the SPR angle that decreases sooner than the predetermined threshold time, and wherein the rate of change of the SPR angle corresponds to a rate of change of adsorption of the analyte to be monitored to the first binding substance.

18. The apparatus of claim 15, wherein the control system is further configured to:
 generate a reflectance curve by measuring the reflectance of the light at each of the plurality of angles over the period of time; and
 determine an SPR reflectance minimum angle from the reflectance curve.

* * * * *

UNITED STATES PATENT AND TRADEMARK OFFICE
CERTIFICATE OF CORRECTION

PATENT NO. : 8,507,294 B2
APPLICATION NO. : 13/500052
DATED : August 13, 2013
INVENTOR(S) : Rahn Page 1 of 1

It is certified that error appears in the above-identified patent and that said Letters Patent is hereby corrected as shown below:

On Title Page 2, Item (56), under "OTHER PUBLICATIONS", in Column 1, Line 14, delete "Poltesrdorf," and insert -- Poltersdorf, --, therefor.

In the Specification

In Column 3, Line 17, delete "angle);" and insert -- angle), --, therefor.

In Column 4, Line 23, delete "Adsoprtion,"" and insert -- Adsorption," --, therefor.

In Column 8, Line 52, delete "sufficient," and insert -- sufficient --, therefor.

In Column 11, Line 45, delete "compound a" and insert -- compound A --, therefor.

In Column 12, Line 40, delete "compound a" and insert -- compound A --, therefor.

In the Claims

In Column 15, Line 16, in Claim 1, delete "surface:" and insert -- surface; --, therefor.

Signed and Sealed this
Nineteenth Day of November, 2013

Teresa Stanek Rea
*Deputy Director of the United States Patent and Trademark Office*